United States Patent [19]

Geier et al.

[11] Patent Number: 5,136,240
[45] Date of Patent: Aug. 4, 1992

[54] AUTOMATICALLY SELF-ADJUSTING EDDY CURRENT PROBE FOR BOLT HOLE INSPECTION

[75] Inventors: Gerard W. Geier, Cincinnati; William L. Herron, West Chester, both of Ohio; Charles M. Brouse, Sr., Richwood, Ky.

[73] Assignee: General Electric Company, Cincinnati, Ohio

[21] Appl. No.: 695,661

[22] Filed: May 6, 1991

[51] Int. Cl.[5] .................... G01N 27/82; G01N 27/72; G01R 33/12
[52] U.S. Cl. .................................................. 324/220
[58] Field of Search ........................ 324/219–221

[56] References Cited

U.S. PATENT DOCUMENTS

| | | | |
|---|---|---|---|
| 4,262,425 | 4/1981 | Sabato | 33/178 R |
| 4,359,905 | 11/1982 | Gavin | 73/644 |
| 4,668,912 | 5/1987 | Junker | 324/220 |
| 4,797,613 | 1/1989 | Wentzell | 324/220 |

*Primary Examiner*—Walter E. Snow
*Attorney, Agent, or Firm*—Jerome C. Squillaro; Charles L. Moore, Jr.

[57] ABSTRACT

A single piece urethane material bolt hole crack detection probe body includes a parallel slot divided head. The head structure permits radial contraction or compression of the head in a parallel manner for axially constant diameter reduction. The structure finds use as an automatically adjustable probe for varying bolt hole sizes.

10 Claims, 1 Drawing Sheet

AUTOMATICALLY SELF-ADJUSTING EDDY CURRENT PROBE FOR BOLT HOLE INSPECTION

BACKGROUND OF THE INVENTION

Rights of the U.S. Government

The invention herein described was made in the performance of work done under Air Force contract #F33657-84-C-0264 awarded by the Department of the U.S. Air Force under which the U.S. Government has certain rights.

This invention relates to eddy current inspection probes for crack detection in bolt holes and the like, and more particularly to a bolt hole eddy current inspection probe inherently compression adjustable in parallel compression for a wide range of bolt hole sizes.

With the advent of high speed turbomachinery such as hot gas turbine engines, for example, aircraft gas turbine engines, a number of critical rotating parts are being specifically tested for cracks and related defects in their bolt hole walls. Structural integrity of critical components requires a high level of defect free parts in their assembly, and various testing equipment have been developed to inspect for metal cracks in critical locations such as bolt hole walls. A particular part may have a number of groups of bolt holes in different ranges of sizes. Consequently a large number of different size probes are required for complete inspection, or the inspector must adjust or shim a probe to fit a particular size hole with a readjustment of the probe to properly fit another hole. Obviously bolt hole inspection may become a complex and time consuming practice. It is highly desirable for an inspector to have an automatically self-adjusting probe which fits a wide variance of bolt hole sizes.

OBJECTS OF THE INVENTION

Accordingly, it is an object of this invention to provide an automatically self-adjusting bolt hole defect detection probe.

It is another object of this invention to provide an automatically self-adjusting bolt hole crack detection probe which reverts to its assigned or original size after bolt hole inspection.

It is yet another object of this invention to provide an automatically self-adjusting bolt hole crack detection eddy current probe utilizing inherent material flexibility instead of mechanical means for parallel adjustment.

SUMMARY OF THE INVENTION

An eddy current probe comprises a probe body of a synthetic resin together with a parallel compression slot divided head which incorporates an electrical eddy current sensing unit therein. The slot divided head compresses in a manner that the unit will be appropriately oriented and biased into engagement with bolt hole walls in a wide range of bolt hole sizes without interim readjustment.

This invention will be better understood when taken in connection with the following drawings and description.

DESCRIPTION OF A PREFERRED EMBODIMENT

Figure 1:
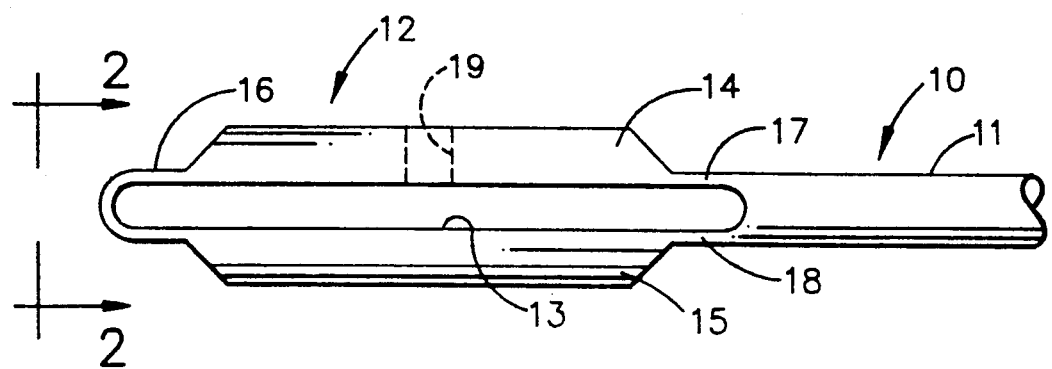
FIG. 1 is a side elevational view of one embodiment of this invention.

Referring now to FIG. 1, probe 10 comprises a shaft section 11 with an enlarged axially extending head 12 of a rounded cross-section larger than the cylindrical cross-section of shaft 11. An important feature of the probe of this invention is the provision of a parallel wall axial slot 13 which not only separates head 12 to define a pair of spaced apart opposed sections 14 and 15, but also provides a remaining elongated web section 16 which joins head sections 14 and 15 to each other at their outer end in a restraining but relative motion permitting manner. Slot 13 also has one end extending axially into shaft 11 to define a pair of upper and lower support strips 17 and 18 each joined to a head section 14 and 15, respectively. Support strips 17 and 18 also join head sections 14 and 15 in a restraining but motion permitting manner. Web section 16 is elongated and curved or coiled to project axially from head section 12 and remain out of slot 13 while at the same time having its flexing characteristics correlated with those of strips 17 and 18. This correlation is achieved by appropriate dimensioning of the parts so that each contributes proportionality towards maintaining the parallel aligned relationship under head compression. In each instance the motion permitting manner of band 16 and strips 17 and 18 permit head sections 14 and 15 to move perpendicularly toward and away from each other while maintaining their parallel and aligned relationship, and accommodating the usual transient irregular motions associated with the probe head adjusting itself to the bolt hole. Also band 16 and support strips 17 and 18 are appropriately sized to return head sections 14 and 15 to their original spacing upon removal of the probe from a bolt hole. The relationship of band 16 to head parts 14 and 15 is more clearly shown in FIG. 2.

Figure 2:
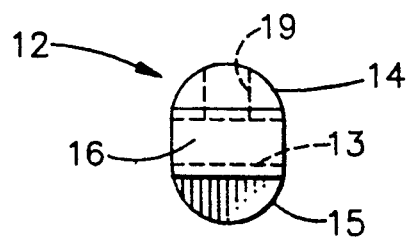
FIG. 2 is a head end view of the probe of FIG. 1 taken along the line 2—2 of FIG. 1.

Referring now to FIG. 2, spaced head parts 14 and 15 are shown joined to each other by a single wide band strip 16 which lends lateral stability to head parts 14 and 15. An appropriate cavity may be formed in head part 14 to contain an eddy current coil or sensor unit 19 therein and may be a form fit cavity for more positive retention of unit 19 in the probe. The arcuate and opposed outer surfaces of head parts 14 and 15 provide ease of insertion, rotation, and withdrawal of the probe from a bolt hole while maintaining a satisfactory degree of closeness of sensor unit 19 to the sidewall of bolt holes of different diameters.

As illustrated in FIG. 2, probe head 12 does not fully circumferentially engage a cylindrical bolt hole. Head section 12 will engage a cylindrical bolt hole at diametrically opposed arcuate regions corresponding to the rounded or semicircular parts of sections 14 and 15 with sensor unit 19 being centrally exposed in one of the opposed arcuate regions. Sensor unit 19, shown in phantom lines in FIG. 1, may be one of a number of well known eddy current sensor units and is positioned in probe head part 14 to generate a favorable electric field extending from the unit into an adjacent bolt hole wall where wall discontinuities such as cracks provide a clearly measurable change in electrical characteristics of the coil.

An important feature of the probe of this invention is the material of its manufacture, a synthetic resin, for example, a urethane rubber. Synthetic resins such as urethane resins and elastomers are available in a wide range of desirable characteristics of flexibility, compressibility and structural integrity. One example includes polyurethane rubbers which are used for various molded and extruded parts including stress bearing components. Probe 10 is adapted to be inserted into a cylindrical aperture bolt hole so that the head sections 14 and 15 are biased into engagement with the hole wall through flexibility of band 16 and support strips 17 and 18. As a consequence, eddy current sensor unit 19 is closely adjacent the bolt hole wall so that, in the usual operation of eddy current probes, the desired electrical current characteristics of the eddy current coil sensor unit 19 are significantly affected by any defect discontinuities in the bolt hole wall, an incipient crack, for example. By this practice, a clear crack caused electrical signal is obtained from the appropriate measuring instrument. For optimum effectiveness, head 12 should have a close fit in a bolt hole, and preferably be useable with a close fit in a range of bolt hole sizes. Probe 10 of this invention accomplishes the latter purpose by the combination of its preferred synthetic resin, e.g. urethane rubber material and its illustrated two part head structure with its dividing parallel compression slot. The described combination permits head sections 14 and 15 to be moved towards each other in a spaced parallel manner for a constant diameter reduction axially along the probe head, a desirable condition for bolt hole inspection, and one that optimally positions sensor unit 19 for crack detection. When the probe is withdrawn from a bolt hole in its compressed state, it quickly returns to its original uncompressed state and size and is available for reuse in a further bolt hole of a diameter different from that of the just inspected hole. Urethane rubbers combine a high degree of structural integrity with excellent flexibility. Moreover, the material exhibits good memory characteristics which, after flexion or compression, enables the urethane structure, particularly head 12, to return to its original configuration and size.

The entire probe is appropriately produced as a single piece urethane rubber material body and may be appropriately molded so that strap 16 and bridging parts or strips 17 and 18 are integral parts of their joining components of the shaft section and head sections 14 and 15. Also, a urethane rubber material is amenable to a machining procedure so that, after molding, the probe may be machined to its predetermined size. A preferred molded probe of this invention includes an appropriately molded cavity for mounting of the eddy current coil sensor unit 19 as well as its electrical connections. Electrical connectors for external instrumentation may also be molded into the probe body.

The probe of this invention, with its inherently wider range of adjustability and its quick return, obviates a prior practice of mechanically adjusting a probe to fit each bolt hole to be inspected which not only requires an inordinate amount of time, but also limits a probe to a limited number of varying diameter bolt holes within its usually limited range of adjustability.

Furthermore, the probe of this invention represents an improved automatic or self-adjusting bolt hole crack detector probe for both, bolt holes of varying diameters and for different sets of holes of different diameters without need for the operator to utilize a number of probes or to readjust the probe between hole inspections. The parallel compression characteristic of head 12 also provides a more constant bias for sensor unit 19 and proper orientation of sensor unit 19 adjacent a bolt hole wall over a wide range of bolt hole sizes.

While this invention has been disclosed and described with respect to a preferred embodiment, it will be understood by those skilled in the art that various changes and modifications may be made without departing from the spirit and scope of the invention in the following claims.

What is claimed:

1. An eddy current probe particularly adapted for metallic component bolt hole defect inspection comprising in combination
   (1) a probe shaft member of a rubber material,
   (2) an enlarged generally rounded and axially extending probe head of said material positioned coaxially at one end of said shaft member,
   (3) said rounded and axially extending head having a central axial parallel wall slot formed substantially completely through said head and extending therein from adjacent an outer end of said head and into said shaft member,
   (4) said slot defining and separating said head into a pair of opposed axially extending head sections of generally semi-circle cross-section in spaced apart parallel relationship with an elongated reduced cross-section band interconnecting said head sections at the head outer end,
   (5) said slot extending axially into said shaft member to define opposed and reduced cross-section support strips joining said head section to said shaft member, and
   (6) said elongated band and said support strips in combination with said rubber material adapted to react to radial compression forces on said head sections to move said head sections towards each other to compress said parallel wall slot in parallel wall relationship to reduce the diameter of said head in an axially constant manner.

2. The invention as recited in claim 1 wherein said probe comprises a urethane rubber material.

3. The invention as recited in claim 1 wherein an electrical eddy current sensing unit is centrally positioned in the semicircular part of one of said head sections for transverse electrical field generation.

4. The invention as recited in claim 1 wherein said elongated band projects axially from the head end of said probe.

5. The invention as recited in claim 1 wherein said elongated band and said support strips are dimensionally correlated to provide proportionate contributing flexibility to the said parallel wall relationship.

6. The invention as recited in claim 1 wherein said band sections are adapted to engage a cylindrical bolt hole wall at diametrically opposite arcuate regions.

7. The invention as recited in claim 1 wherein said elongated band and said support strips comprise the same material as said head and shaft sections.

8. The invention as recited in claim 7 wherein said material is a synthetic rubber.

9. The invention as recited in claim 7 wherein said material is a urethane rubber.

10. The invention as recited in claim 7 wherein said probe member and said elongated band and said support strips constitute a single piece construction.

* * * * *